United States Patent
Stone et al.

(10) Patent No.: US 9,372,916 B2
(45) Date of Patent: Jun. 21, 2016

(54) DOCUMENT TEMPLATE AUTO DISCOVERY

(71) Applicant: athenahealth, Inc., Watertown, MA (US)

(72) Inventors: Steven James Stone, Urbana, IL (US); Frederick Henle, Suffield, CT (US); Fuchang Yin, Waltham, MA (US)

(73) Assignee: athenahealth, Inc., Watertown, MA (US)

( * ) Notice: Subject to any disclaimer, the term of this patent is extended or adjusted under 35 U.S.C. 154(b) by 664 days.

(21) Appl. No.: 13/714,849

(22) Filed: Dec. 14, 2012

(65) Prior Publication Data

US 2014/0173422 A1 Jun. 19, 2014

(51) Int. Cl.
*G06F 17/21* (2006.01)
*G06F 17/30* (2006.01)
*G06K 9/00* (2006.01)
*G06F 17/24* (2006.01)
*G06F 19/00* (2011.01)

(52) U.S. Cl.
CPC .......... *G06F 17/3061* (2013.01); *G06F 19/328* (2013.01); *G06K 9/00442* (2013.01); *G06K 9/00449* (2013.01); *G06F 19/322* (2013.01)

(58) Field of Classification Search
CPC ................................. G06F 17/24; G06F 17/21
USPC .......................................................... 715/244
See application file for complete search history.

(56) References Cited

U.S. PATENT DOCUMENTS

| | | | |
|---|---|---|---|
| 4,858,121 A | 8/1989 | Barber et al. | |
| 5,253,164 A | 10/1993 | Holloway et al. | |
| 6,076,066 A | 6/2000 | Dirienzo et al. | |
| 6,208,973 B1 | 3/2001 | Boyer et al. | |
| 6,341,265 B1 | 1/2002 | Provost et al. | |
| 6,343,271 B1 | 1/2002 | Peterson et al. | |
| 7,016,856 B1 | 3/2006 | Wiggins | |
| 7,039,856 B2 | 5/2006 | Peairs et al. | |
| 7,447,988 B2 | 11/2008 | Ross | |
| 8,233,714 B2 | 7/2012 | Zuev et al. | |
| 2002/0032584 A1 | 3/2002 | Doctor et al. | |
| 2005/0108001 A1 | 5/2005 | Aarskog | |
| 2007/0168382 A1 | 7/2007 | Tillberg et al. | |
| 2007/0179814 A1* | 8/2007 | Hernandez et al. | 705/3 |
| 2010/0094657 A1* | 4/2010 | Stern | G06F 19/322 705/3 |
| 2010/0306218 A1* | 12/2010 | Bacon | G06F 19/324 707/759 |
| 2011/0196704 A1* | 8/2011 | Mansour | 705/3 |

(Continued)

OTHER PUBLICATIONS

U.S. Appl. No. 60/203,315, filed May 10, 2000, Ross.

(Continued)

*Primary Examiner* — James J Debrow
(74) *Attorney, Agent, or Firm* — Wolf, Greenfield & Sacks, P.C.

(57) ABSTRACT

Methods and apparatus for generating a template for automatic data capture are described. The method comprises determining locations of a plurality of data fields in a first document, wherein the plurality of data fields are identified based, at least in part, on structured data associated with the first document, identifying at least one second document that includes the plurality of data fields in locations similar to those determined for the first document to produce a set of documents, determining locations of a plurality of anchorboxes describing common text elements of the set of documents, and generating the template, wherein the template describes locations of the plurality of anchorboxes and locations of the plurality of data fields.

21 Claims, 12 Drawing Sheets

(56) References Cited

U.S. PATENT DOCUMENTS

| | | | |
|---|---|---|---|
| 2012/0109686 A1* | 5/2012 | Higbie et al. ............... | 705/3 |
| 2014/0214450 A1 | 7/2014 | Bechtold et al. | |

OTHER PUBLICATIONS

Civil Action No. 1:11-cv-11260-GAO, PC-ACE Users Manual HCFA 1500, Release 4.30 Aug. 1996.2 pages.

Civil Action No. 1:13-cv-10794-IT, athenahealth, Inc.'s Opening Claim Construction Brief, dated Jun. 27, 2014, filed Jun. 27, 2014. 23 pages.

Civil Action No. 1:13-cv-10794-IT, athenahealth, Inc.'s Proposed Claim Constructions and Support, dated Apr. 25, 2014, filed Apr. 25, 2014. 7 pages.

Civil Action No. 1:13-cv-10794-IT, athenahealth, Inc.'s Preliminary Identification of Claim Terms to be Construed, dated Apr. 11, 2014, filed Apr. 11, 2014. 3 pages.

Civil Action No. 1:13-cv-10794-IT, athenahealth, Inc.'s Replacement Claim Construction Reply Brief, dated Sep. 5, 2014, filed Sep. 10, 2014. 15 pages.

Civil Action No. 1:13-cv-10794-IT, CareCloud Corporation's Claim Construction Sur-Reply Brief, dated Oct. 6, 2014, filed Oct. 6, 2014. 16 pages.

Civil Action No. 1:13-cv-10794-IT, CareCloud Corporation's Identification of Claim Terms/Phrases for Construction, dated Apr. 11, 2014, filed Apr. 11, 2014. 4 pages.

Civil Action No. 1:13-cv-10794-IT, CareCloud Corporation's Preliminary Invalidity Contentions, dated Jan. 10, 2014, filed Jan. 10, 2014. 106 pages.

Civil Action No. 1:13-cv-10794-IT, CareCloud Corporation's Responsive Claim Construction Brief, dated Aug. 1, 2014, filed Aug. 1, 2014. 24 pages.

Civil Action No. 1:13-cv-10794-IT, Declaration of Chi Cheung in Support of CareCloud Corporation's Responsive Claim Construction Brief, .dated Aug. 1, 2014, filed Aug. 1, 2014. 40 pages.

Civil Action No. 1:11-cv-11260-GAO, "Advanced Billing Features," webpage found at http://web.archive.org/web/19981202203523/http://www.medicalmanager.com/v9/004.htm. 6 pages.

Civil Action No. 1:11-cv-11260-GAO, "Customization," webpage found at http://web.archive.org/web/19981205131953/http://www.medicalmanager.com/v9/007.htm . 3 pages.

Civil Action No. 1:11-cv-11260-GAO, "Electronic Communications," webpage found at http://web.archive.org/web/19981206025311/http://www.medicalmanager.com/v9/003.htm. 4 pages.

Civil Action No. 1:11-cv-11260-GAO, "Executive Summary," webpage found at http://web.archive.org/web/19990221040230/http://www.medicalmanager.com/v9/summary.htm. 6 pages.

Civil Action No. 1:11-cv-11260-GAO, "Introduction," webpage found at http://web.archive.org/web/19981205002805/http://www.medicalmanager.com/v9/intro.htm. 1 page.

Civil Action No. 1:11-cv-11260-GAO, "Patient Entry and Billing Cycles," webpage found at http://web.archive.org/web/19981206004426/http://www.medicalmanager.com/v9/002.htm. 6 pages.

Civil Action No. 1:11-cv-11260-GAO, Corrected Request for Ex Parte Reexamination of U.S. Pat. No. 6,343,271. Nov. 14, 2011. 1487 pages.

Civil Action No. 1:11-cv-11260-GAO, "Data Dictionary," webpage found at http://www.imaxsoft.com/docs/99%20Other%20Manuals/03%20IMAXSOFT%20Other%20Products/DOOR/DOOR%20V1_0/PDF/Facets%20Doc/FACETS/SA_REF.PDF; Facets Data Dictionary User Guide, Release 2.8. Dec. 1998. 73 pages.

Civil Action No. 1:11-cv-11260-GAO, Facets EDI 837 Outbound Claims Submission Subsystem User Guide, Release 2.8. Dec. 1998. 192pages.

Civil Action No. 1:11-cv-11260-GAO, Facets Internet Applications Reference Guide, Release 2.8, Dec. 1998. webpage found at http://www.imaxsoft.com/docs/99%20Other%20Manuals/03%20IMAXSOFT%20Other%20Products/DOOR/DOOR%20V1_0/PDF/Facets%20Doc/FACETS/UPDATE.PDF. 74 pages.

Civil Action No. 1:11-cv-11260-GAO, Facets Product Overview, Fall 1997, webpage found at http://www.imaxsoft.com/docs/99%20Other%20Manuals/03%20IMAXSOFT%20Other%20Products/DOOR/DOOR%20V1_0/PDF/Facets%20Doc/FACETS/OVERVIEW.PDF. 42 pages.

Civil Action No. 1:11-cv-11260-GAO, Facets User Guide: System Administration Reference, webpage found at http://www.imaxsoft.com/docs/99%20Other%20Manuals/03%20IMAXSOFT%20Other%20Products/DOOR/DOOR%20V1_0/PDF/Facets%20Doc/FACETS/INTERNET.PDF. 134 pages.

Civil Action No. 1:11-cv-11260-GAO, Facets User Guide: System Administration Processing, webpage found at http://www.imaxsoft.com/docs/99%20Other%20Manuals/03%20IMAXSOFT%20Other%20Products/DOOR/DOOR%20V1_0/PDF/Facets%20Doc/FACETS/INTERNET.PDF. 306 pages.

Civil Action No. 1:11-cv-11260-GAO, Facets Product Update, Release 2.81, Mar. 1999, webpage found at http://www.imaxsoft.com/docs/99%20Other%20Manuals/03%20IMAXSOFT%20Other%20Products/DOOR/DOOR%20V1_0/PDF/Facets%20Doc/FACETS/EDI837O.PDF. 394 pages.

Civil Action No. 1:11-cv-11260-GAO, Claimsnet.com Form 424B1, filed Apr. 8, 1999. 88 pages.

Civil Action No. 1:11-cv-11260-GAO, "Brochures," including all Brochure Index Links, http://web.archive.org/web/19980112180618/http://www.claimsnet.com/brochures/default.htm. 15 pages.

Civil Action No. 1:11-cv-11260-GAO, Medical Manager Corp. 1998 10-K, filed Mar. 23, 1999. 113 pages.

Civil Action No. 1:11-cv-11260-GAO, "Halley Exchange Demo Software," webpage found at http://web.archive.org/web/19971008140858/http://www.halley.com/intface.htm ("Halley Demo"). 5 pages.

Civil Action No. 1:11-cv-11260-GAO, "Halley Generated Reporting," (Complete Sample Reports), webpage found at http://web.archive.org/web/19971008140908/http://www.halley.com/hrept5.htm. 25 pages.

Civil Action No. 1:11-cv-11260-GAO, "Halley Exchange Demo Software," webpage found at http://web.archive.org/web/19971008140858/http://www.halley.com/intface.htm. (Native format). 1 page.

Civil Action No. 1:11-cv-11260-GAO, "Halley Reporting," webpage found at http://web.archive.org/web/19971008140908/http://www.halley.com/hrept5.htm. 2 pages.

Civil Action No. 1:11-cv-11260-GAO, "Halley Interface," webpage found at http://web.archive.org/web/19971008140858/http://www.halley.com/intface.htm. 4 pages.

Civil Action No. 1:11-cv-11260-GAO, "Halley Homepage," webpage found at http://web.archive.org/web/19971008140814/http://www.halley.com/ . 2 pages.

Civil Action No. 1:11-cv-11260-GAO, "Halley Overview," webpage found at http://web.archive.org/web/19971008140840/http://www.halley.com/overview.htm. 2 pages.

Civil Action No. 1:11-cv-11260-GAO, "Halley Exchanges," vol. 2, Winter 1996-1997, webpage found at http://web.archive.org/web/19971008141453/http://www.halley.com/nlett2.htm . 5 pages.

Civil Action No. 1:11-cv-11260-GAO, "Halley Reasons," webpage found at http://web.archive.org/web/19971008140848/http://www.halley.com/reason.htm . 2 pages.

Civil Action No. 1:11-cv-11260-GAO, Medicode, Inc.'s Amendment No. 2 to Form S-1, filed Nov. 18, 1997 ("Medicode 1997 S-1/A"). 133 pages.

Civil Action No. 1:11-cv-11260-GAO, "Medicode Overview," http://web.archive.org/web/19980626131906/http://www.medicode.com/html/aboutmedicode.html. 3 pages.

(56) References Cited

OTHER PUBLICATIONS

Civil Action No. 1:11-cv-11260-GAO, Webpage found at http://web.archive.org/web/12980626132238/http://www.medicode.com/index.html. 1 page.

Civil Action No. 1:11-cv-11260-GAO, "Claims Manager Overview," webpage found at http://web.archive.org/web/19980626132425/http://www.medicode.com/html/claimsmanager.html. 2 pages.

Civil Action No. 1:11-cv-11260-GAO, AFEHCT Presentation to HCFA, Jan. 14, 1997, webpage found at http://web.archive.org/web/19990202033335/http://www.afehct.org/information_library.html . 113 pages.

Civil Action No. 1:11-cv-11260-GAO, "Software Qtiestions," webpage found at http://web.archive.org/web/19970411063248/http://www.claimsnet.com/html/claims_processor_questions.htm. 4 pages.

Civil Action No. 1:11-cv-11260-GAO, "Sample Claims," webpage found at http://web.archive.org/web/19970411063339/http://www.claimsnet.com/html/sample_claims.htm. 1 page.

Civil Action No. 1:11-cv-11260-GAO, "Medical Services," webpage found at http://web.archive.org/web/19970411062445/http://www.claimsnet.com/html/medical_services.htm. 1 page.

Civil Action No. 1:11-cv-11260-GAO, "About Claimsnet," webpage found at http://web.archive.org/web/19970411062358/http://www.claimsnet.com/html/about_american_net_claims.htm. 1 page.

Civil Action No. 1:11-cv-11260-GAO, "Steps," webpage found at http://web.archive.org/web/19970411062637/http://www.claimsnet.com/htm1/7_easy_steps.htm. 1 page.

Civil Action No. 1:11-cv-11260-GAO, "Demo," webpage found at http://web.archive.org/web/19970411062653/http://www.claimsnet.com/html/claims_processor_demo.htm, including all linked steps of the demo. 6 pages.

Civil Action No. 1:11-cv-11260-GAO, "Erisco Overview," webpage found at http://web.archive.org/web/19971017134753/http://www.erisco.com/prdorvw.htm. 2 pages.

Civil Action No. 1:11-cv-11260-GAO, "Questions," webpage found at http://web.archive.org/web/19970411063301/http://www.claimsnet.com/html/claimsnet.com_questions.htm. 3 pages.

Civil Action No. 1:11-cv-11260-GAO, Health Data Directory. Bill Briggs ed. Faulkner & Gray 2000 ed. 1999. 212 pages.

Civil Action No. 1:11-cv-11260-GAO, "Electronic Claims," http://web.archive.org/web/20000303032008/http://www.accumedic.com/ele.htm . 1 page.

Civil Action No. 1:11-cv-11260-GAO, "HCIS Products," http://web.archive.org/web/20000301143435/http://www.hcis.com/products/index.htm. 3 pages.

Civil Action No. 1:11-cv-11260-GAO, Webpage found at http://web.archive.org/web/20000303084813/http://www.accumedic.com/index.htm. 1 page.

Civil Action No. 1:11-cv-11260-GAO, Webpage found at http://web.archive.org/web/20000517042344/http://www.hcis.com/index.htm. 1 page.

Civil Action No. 1:11-cv-11260-GAO, "VISION HomeCare Overview," Webpage found at ttp://web.archive.org/web/20000523231231/http://www.hcis.com/products/vision_descrip.htm. 2 pages.

Civil Action No. 1:11-cv-11260-GAO, PC-ACE Users Manual HCFA 1500, Release 4.30 Aug. 1996. 272 pages.

Civil Action No. 1:11-cv-11260-GAO, TX-ACE Users Manual HCFA 1500, Release 6.0 Jan. 1996. 284 pages.

Civil Action No. 1:11-cv-11260-GAO, Core Module Manual, Release 10.04. Jan. 2001. 1083 pages.

Civil Action No. 1:11-cv-11260-GAO, MedicWare Interface Manual, Release 10.03 Jul. 2001. 39 pages.

Civil Action No. 1:11-cv-11260-GAO, Technical Services Bulletin: Service Pack 2 SP2. May 7, 2001. 5 pages.

Civil Action No. 1:11-cv-11260-GAO, New Client Assistance Manual Oct. 2000. 99 pages.

Civil Action No. 1:11-cv-11260-GAO, ClickON Technology Brochure. 2 pages.

* cited by examiner

→ General Hospital    2/3/2011  9:42:37 AM   PAGE   1/001   Fax Server

General Hospital

| | | |
|---|---|---|
| Patient: | CARBONE, DOLORES | Acc#: 762184 |
| MRN: | 031722 | Sex: F |
| DOB: | 07/26/1945 | Pat Location: MM |
| Account#: | 13658826 | Date of Service: 02/02/2011 |

Exam: BDMSCR - DIGITAL MAMMO BIL SCREEN
Requesting Provider:  MCFARLAND, DUDLEY, MD
Attending Provider:   MCFARLAND, DUDLEY, MD
Signs and Symptoms:   MAMMOGRAM SCREENING This digital full field study is compared to the 12/01 examination and computer-aided detection was utilized as a second reader.

Skin calcifications are seen. No suspicious cluster of microcalcifications is evident. No mass or architectural distortion is seen. Little glandular tissue is present.
IMPRESSION: Unremarkable study without significant interval change.

BI-RADS CATEGORY 2 - BENIGN                LETTER #1

NELSON BOGARD, M.D./rl

Code: 77052, G0202

FIG. 3

```
General Hospital    2/3/2011 9:42:37 AM    PAGE    1/001    Fax Server
```

General Hospital

↗ 300

| | | | |
|---|---|---|---|
| Patient: | CARBONE, DOLORES ⟵510 | Acc#: | 762184 |
| MRN: | 031722 | Sex: | F |
| DOB: | 07/26/1945 ⟵512 | Pat Location: | MM |
| Account#: | 13658826 | Date of Service: | 02/02/2011 |

⟵514

Exam: BDMSCR – DIGITAL MAMMO BIL SCREEN
Requesting Provider: MCFARLAND, DUDLEY, MD
Attending Provider: MCFARLAND, DUDLEY, MD
Signs and Symptoms: MAMMOGRAM SCREENING This digital full field study is compared to the 12/01 examination and computer-aided detection was utilized as a second reader.

Skin calcifications are seen. No suspicious cluster of microcalcifications is evident. No mass or architectural distortion is seen. Little glandular tissue is present.
IMPRESSION: Unremarkable study without significant interval change.

BI-RADS CATEGORY 2 - BENIGN                LETTER #1

NELSON BOGARD, M.D./rll

Code: 77052, G0202

FIG. 5

Birth Date: 08/0⬛/19⬛⬛
Account #: 12368⬛⬛⬛
Exam #: 709⬛⬛⬛
Exam Date: 08/1⬛/2011, 1⬛:⬛⬛:00
Patient Sex: M Exam Code/Description: EX CHEST2 - CHEST 2 V ⬛⬛⬛⬛⬛⬛⬛⬛⬛

FIG. 6

General Hospital   2/3/2011 9:42:37 AM   PAGE   1/001   Fax Server

General Hospital

| | |
|---|---|
| Patient: CARBONE, DOLORES | Acc#: 762184 |
| MRN: 031722 | Sex: F |
| DOB: 07/26/1945 | Pat Location: MM |
| Account#: 13658826 | Date of Service: 02/02/2011 |

Exam: BDMSCR - DIGITAL MAMMO BIL SCREEN
Requesting Provider: MCFARLAND, DUDLEY, MD
Attending Provider: MCFARLAND, DUDLEY, MD
Signs and Symptoms: MAMMOGRAM SCREENING This digital full field study is compared to the 12/01 examination and computer-aided detection was utilized as a second reader.

Skin calcifications are seen. No suspicious cluster of microcalcifications is evident. No mass or architectural distortion is seen. Little glandular tissue is present.
IMPRESSION: Unremarkable study without significant interval change.

BI-RADS CATEGORY 2 - BENIGN                     LETTER #1

NELSON BOGARD, M.D./rll

Code: 77052, G0202

PharmacyLand, Inc. — 948
Prescription Refill Request — 950

Date: 12/05/2012                                                              Time: 9:15 AM
930
Prescriber Information:
Physician:    JEFFERY SEVER — 920                           Phone: 888-555-1212
932  Address:    311 ARSENAL STREET                            Fax: 888-555-1234
              WATERTOWN, MA 02472                              DEA #:
934
Patient Information:                                                                      916
936  Patient:    CHARLOTTE DORFMAN — 910              Birthdate: 10/17/1961
     Address:    123 MAIN ST. — 912                      Med Record #:
938              ANYTOWN, USA 00000 — 914                     Phone: 888-555-6789
                                                                                              918

Prescription Information:
940  Rx Number:   286753-02272                    Requested P/U Time: 12/05/2012 08:00AM
     Drug:        POTASSIUM CL 20MEQ ER TABLETS     Prescribed Qty: 720
     Generic For:                                  Last Refill: 07/05/2012
     Sig:         TAKE 4 TABLETS BY MOUTH TWICE DAILY
                  AS DIRECTED Message:

☐ Denied
☐ If there are NO changes to the Rx please         If there ARE changes to the Rx please
  circle TOTAL # of Authorized Refills:             check box and write in changes.
  PRN  6  5  4  3  2  1                            ☐ Drug: _____
                                                   ☐ Directions: _____

☐ Authorized as a 90 day supply
  PLUS # of additional Refills:
  PRN  3  2  1  0
                                                   ☐ Refills: _____  ☐Qty: _____

Authorized by: _____

In accordance with state regulations, a generic will be substituted unless otherwise indicated.
☐ Dispense as Written/Brand Medically Necessary 942
       The DEA prohibits the use of this form for a controlled substance medication. Please contact
944          the pharmacy with a new prescription if you wish the patient to continue this medication.

This communication is intended for the use of the person or entity by whom it is addressed and may contain information that is privileged and confidential, the disclosure
of which is governed by applicable law. If the reader of this message is not the intended recipient, or the employee or agent responsible for delivering it to the intended
recipient, you are hereby notified that any dissemination, distribution, or copying of this information is strictly prohibited. If you have received this message in error,
please notify sender immediately.
                                                                                              946

FIG. 9

PRIOR AUTHORIZATION REQUEST FORM

AUTO-FAX ELECTRONICALLY TRANSMITTED: 11-12-2012 14:56

PRIOR AUTHORIZATION REQUIRED – ACTION REQUIRED

As the prescriber, this patient's insurance company requires that a prior authorization is completed for this prescription. Your patient and our pharmacy appreciate your assistance in obtaining the prior authorization by using the contact method below:

PA Fax #
Action Taken:

PA Authorization # _____  PA Authorized as of _____  Denied _____

PRESCRIBER INFORMATION:
- Name: KEN REINHART
- Address: 311 ARSENAL STREET, WATERTOWN, MA 02472
- Phone: 888-555-1212
- Fax: 888-555-1234

PHARMACY INFORMATION:
- From: MAIN STREET DRUGS
- Address: 500 MAIN STREET, ANYTOWN, USA 00000
- Phone: 888-555-5555
- Fax: 888-555-6677

PATIENT INFORMATION:
- Name: LABRADOR, STANLEY
- DOB: 01-14-1945
- Address: 456 MAIN ST, ANYTOWN, USA 00000
- Phone: 888-555-6789

THIRD PARTY INFORMATION:
- Name: PHARMATECH
- Cardholder ID: 947285744
- Group Number: MASA
- Person Code: 01
- Relationship: 1
- TP Help Desk Phone: 888-555-4321

NEW PRESCRIPTION:
- Medication:
- Quantity:
- Refills:
- SIG:

ORIGINAL PRESCRIPTION:
- Rx #:
- Drug: PRADAXA 150 MG CAPSULE
- Qty. Prescribed: 60.0 EA
- Prescribed Refills: 5
- Date Written: 11-08-2012
- SIG: TAKE ONE CAPSULE BY MOUTH TWICE A DAY

Pharmacy Comments:

Prescriber Comments:

Prescriber's Name (Printed): _____
Transmitted By: _____ (TX ONLY)   Prescriber's DEA # _____
(TX/HI ONLY)   DPS # / Oral Code _____
Prescriber's Signature: _____   Date: _____

Massachusetts Only: Interchange is mandated unless Practitioner writes the words "No Substitution"

The information contained in this electronic message as well as any attachments to this message are intended for the exclusive use of the intended recipient and may contain confidential or privileged information. If you are not the intended recipient, please destroy all copies of this message as well as its attachments and advise the sender immediately.

PRIOR AUTHORIZATION REQUEST FORM

FIG. 10

DOCUMENT TEMPLATE AUTO DISCOVERY

BACKGROUND

The widespread deployment of computer systems in medical practices has encouraged healthcare providers to transition conventional paper-based patient medical records to electronic health records (EHRs—also called electronic medical records, or EMRs) and to communicate medical billing information to payers electronically. To facilitate the management of EMRs and/or medical billing, some medical practices contract with third-party providers of a practice management system. The practice management system may include a web-based interface that enables users at the medical practice to input, view, and interact with stored health information for patients of the medical practice.

Many communications between service providers in the healthcare industry including pharmacies, laboratories, medical practices, and payers such as insurance companies, are transmitted using paper-based techniques such as mail or facsimile. For medical practices that use EMRs to store patient health information, a user often is required to review the received documents and manually enter health information in the received documents into an associated patient's EMR.

SUMMARY

Some medical practices may receive hundreds or thousands of such communications every day and analyzing the information in the received documents takes considerable time and resources. The inventors have recognized and appreciated that the process of analyzing documents received by a medical practice to identify relevant health information may be improved by automatically creating templates for similar documents received from a particular source. The templates may describe locations and/or formats of the relevant health information on the documents to be captured by an automatic data capture system. To this end, some embodiments of the invention are directed to methods and apparatus for automatically generating templates from a plurality of documents received by a practice management system on behalf of a medical practice to facilitate automatic data capture using the templates.

Some embodiments are directed to a method of generating a template for automatic data capture. The method comprises determining, with at least one processor, locations of a plurality of data fields in a first document, wherein the plurality of data fields are identified based, at least in part, on structured data associated with the first document; identifying at least one second document that includes the plurality of data fields in locations similar to those determined for the first document, wherein the first document and the at least one second document form a set of documents; determining locations of a plurality of anchorboxes describing common text elements of the set of documents; and generating the template, wherein the template describes locations of the plurality of anchorboxes and locations of the plurality of data fields.

Some embodiments are directed to a computer system providing a practice management system, the computer system comprising at least one processor programmed to: determine locations of a plurality of data fields in a first document, wherein the plurality of data fields are identified based, at least in part, on structured data associated with the first document; identify at least one second document that includes the plurality of data fields in locations similar to those determined for the first document, wherein the first document and the at least one second document form a set of documents; determine locations of a plurality of anchorboxes describing common text elements of the set of documents; and generate the template, wherein the template describes locations of the plurality of anchorboxes and locations of the plurality of data fields.

Some embodiments are directed to at least one computer-readable storage medium encoded with a plurality of instructions that, when executed by at least one computer, perform a method. The method comprises determining locations of a plurality of data fields in a first document, wherein the plurality of data fields are identified based, at least in part, on structured data associated with the first document; identifying at least one second document that includes the plurality of data fields in locations similar to those determined for the first document, wherein the first document and the at least one second document form a set of documents; determining locations of a plurality of anchorboxes describing common text elements of the set of documents; and generating a template, wherein the template describes locations of the plurality of anchorboxes and locations of the plurality of data fields.

It should be appreciated that all combinations of the foregoing concepts and additional concepts discussed in greater detail below (provided that such concepts are not mutually inconsistent) are contemplated as being part of the inventive subject matter disclosed herein.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings:

FIG. 3 is an illustrative healthcare document that may be processed in accordance with some embodiments of the invention;

FIG. 5 is the illustrative healthcare document of FIG. 3 on which a plurality of captureboxes have been identified in accordance with some embodiments of the invention;

FIG. 6 is a graphical illustration of a set of overlaid portions of healthcare documents identified in accordance with some embodiments of the invention;

FIG. 7 is the illustrative healthcare document of FIG. 3 on which a plurality of captureboxes and anchorboxes have been identified;

FIG. 9 is another illustrative healthcare document that may be processed in accordance with some embodiments of the invention;

FIG. 10 is another illustrative healthcare document that may be processed in accordance with some embodiments of the invention;

DETAILED DESCRIPTION

The present disclosure generally relates to inventive methods and apparatus for generating templates used to automatically capture data from documents, and more specifically relates to analyzing a set of healthcare documents to generate a template that includes information identifying locations of data fields on the documents for performing data capture. By using templates for automatic data capture, less information in healthcare documents received by a medical practice may need to be manually entered by a user. Automation of the template generation process may further improve efficiency by requiring less resources than would have been required by manually generating at least some of the templates used for automatic data capture.

Some healthcare providers receive large quantities of documents over the course of hours, days, or weeks. Examples of such documents include, but are not limited to, laboratory results, patient referral forms, prescription information, and medical billing information. In some conventional practice management systems, the received documents are classified and information in the documents is manually entered into the practice management system by a user to update the practice management system.

The process of data capture from documents received for a medical practice and processed by a practice management system may be at least partially automated by using templates that describe characteristics of a document and identify one or more locations on the document to perform data capture. When a received document is identified as matching at least some characteristics of a particular template stored by the practice management system, the matching template may be used to perform data capture. The inventors have recognized and appreciated that manually creating templates for data capture from the large volume of documents received by a medical practice is a labor-intensive process that can be improved by analyzing features of sets of received documents with similar characteristics to automatically generate one or more templates used for data capture.

Figure 1:
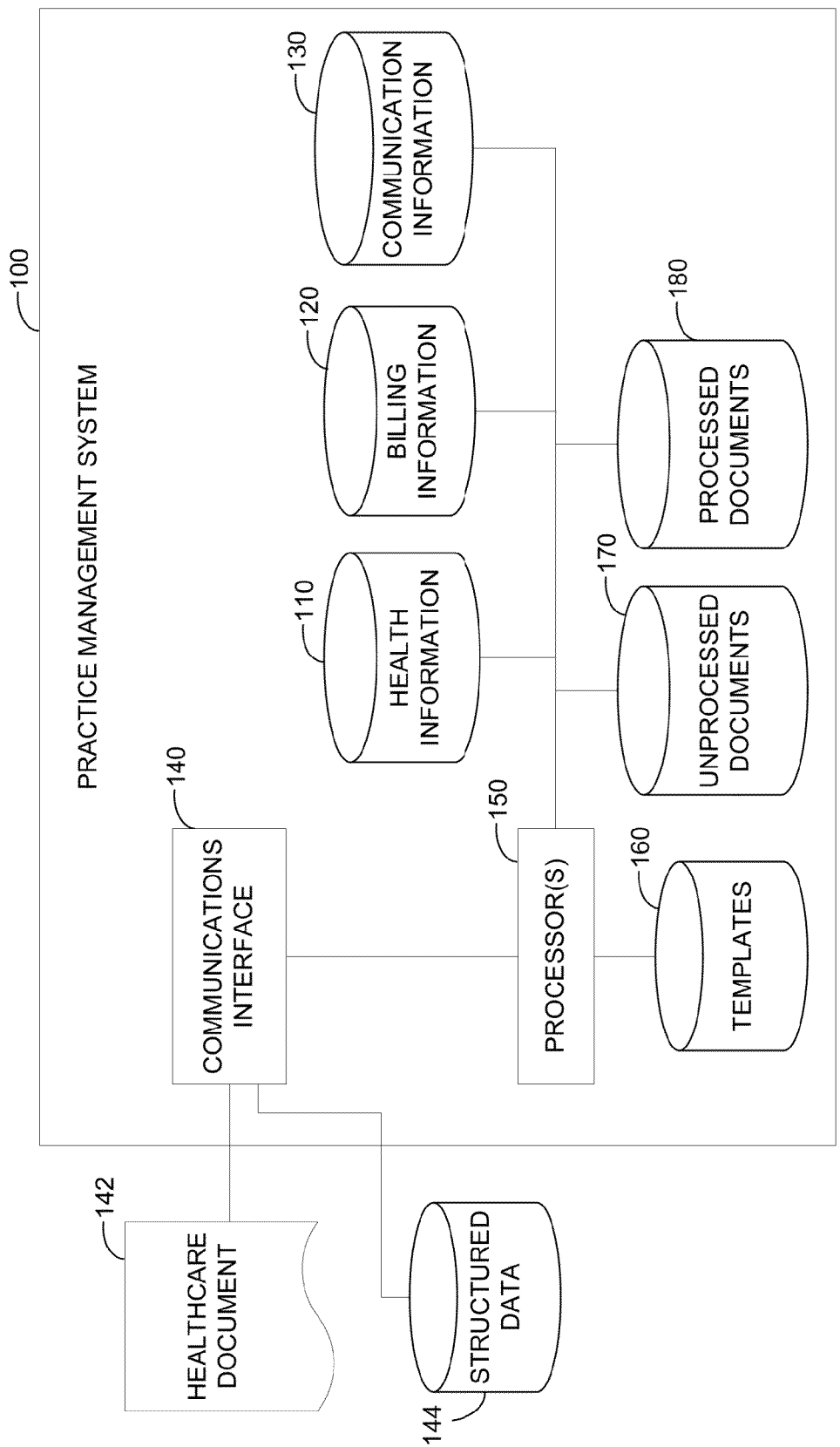
FIG. 1 is a schematic of an illustrative practice management system that may be used in accordance with some embodiments of the invention.

FIG. 1 illustrates an exemplary practice management system that may be used in accordance with some embodiments of the invention. Practice management system 100 may be a networked system that includes a plurality of components configured to perform tasks related to specific functions within the practice management system. The plurality of components are configured to facilitate the management of various aspects of medical practices including, billing, managing health information, and communications with patients.

Exemplary practice management system 100 includes health information component 110, which is configured to store electronic health information for patients at medical practices associated with the practice management system. The electronic health information stored by health information component 110 includes, but is not limited to, electronic medical records, lab results, imaging results, and pay for performance requirements. Health information component 110 may include one or more processors (not shown) programmed to manage the electronic health information stored thereon. For example, one or more processors associated with health information component 110 may be programmed to reconcile data received in a healthcare document with electronic health information stored by health information component 110.

Practice management system 100 also includes billing information component 120, which is configured to facilitate the collection, submission, and tracking of claims filed by medical practices associated with the practice management system to a plurality of payers (including patients). By facilitating interactions between medical practices and payers, billing information component 120 ensures that each medical practice is properly compensated for medical services rendered to patients treated at the medical practices.

Exemplary practice management system 100 also includes communication information component 130, which is configured to interact with health information component 110 and billing information component 120, to facilitate interactions with patients on behalf of a medical practice using a communications channel. The communications sent via the communications channel may include, but are not limited to, text-based communications, web-based communications, and phone-based communications. In some embodiments, communication information component 130 may include a web-based portal implemented as a portion of a web application, with which patients of a medical practice may interact to perform a plurality of actions associated with services at the medical practice including, but not limited to, registering to be a new patient at a medical practice, providing a third party with access to interact with the medical practice, secure messaging of protected health information (PHI) with authorized medical personnel, submitting electronic payment information for medical bills, retrieving laboratory results, accessing educational content, completing medical forms, and receiving directions to the medical practice.

Exemplary practice management system 100 also includes a communications interface 140 configured to communicate via at least one network with one or more sources external to the practice management system. For example, the practice management system 100 may communicate on behalf of a medical practice by sending and/or receiving one or more healthcare documents 142 to/from other service providers in the healthcare industry including, but not limited to, pharmacies, laboratories, and payers such as insurance companies.

Communications interface 140 may receive communications (including healthcare documents 142) from service providers in any suitable format (e.g., fax, email or other electronic transmission) and the techniques described herein are not limited by the particular format in which healthcare documents are received from service providers. In some embodiments, communications interface 140 receives healthcare documents 142 from service providers using a fax interface configured to receive facsimile transmissions. In addition to receiving healthcare documents from service providers, communications interface 140 may also be configured to receive structured data 144 associated with one or more healthcare documents 142. In some embodiments, the structured data 144 may describe information in an associated healthcare document 142 that was manually entered by a user and the structured data 144 may be used to generate one or more templates for automatic data capture, as discussed in more detail below.

Healthcare documents 142 received by practice management system 100 may be processed using one or more processors 150 programmed to analyze one or more characteristics of the received healthcare documents 142. In some embodiments, practice management system 100 includes a repository of templates 160 configured to facilitate automatic data capture from healthcare documents 142 received from a service provider. As discussed in more detail below, a received healthcare document 142 may be compared to the templates stored in template repository 160 to determine whether the received document includes characteristics matching characteristics associated with one of the templates. Healthcare documents 142 that match a particular template 160 are processed using the matching template to automatically capture data from the document. In some embodiments, the automatically-captured data may be stored by one or more components of practice management system 100. For example, the captured data may be stored as health information by health information component 110.

Practice management system 100 may also include one or more datastores such as unprocessed document datastore 170 configured to store received healthcare documents to which a template has not been applied and processed document datastore 180 configured to store received healthcare documents to which a template has been applied. In some embodiments, unprocessed document datastore 170 and processed document datastore 180 may alternatively or additionally be configured to store one or more electronic images associated with received healthcare documents 142.

Although exemplary practice management system 100 is illustrated as having two datastores for separately storing received healthcare documents 142 based on whether the documents were processed using a template, any number of datastores, including a single datastore, may alternatively be used to store healthcare documents 142 received by practice management system 100 and the illustrated embodiment in FIG. 1 is merely one example of such a system. In some embodiments that include a single datastore for storing received healthcare documents 142, stored healthcare documents may be associated with an indication, such as metadata, describing whether the document was processed using a template.

It should be appreciated that practice management system 100 may include any suitable number of components that interact in any suitable way, and the illustrative embodiment shown in FIG. 1 is merely provided to describe one example system. Furthermore, some or all of the components in practice management system 100 may interact by sharing data, triggering actions to be performed by other components, preventing actions from being performed by other components, storing data on behalf of other components, and/or interacting in any other suitable way.

In some embodiments, communications interface 140 may be included as a portion of one or more of health information component 110, billing information component 120, and communication information component 130, and the techniques described herein are not limited in the particular manner in which each of the components of practice management system 100 is configured to receive information about healthcare documents 142 from an external source.

Figure 2:
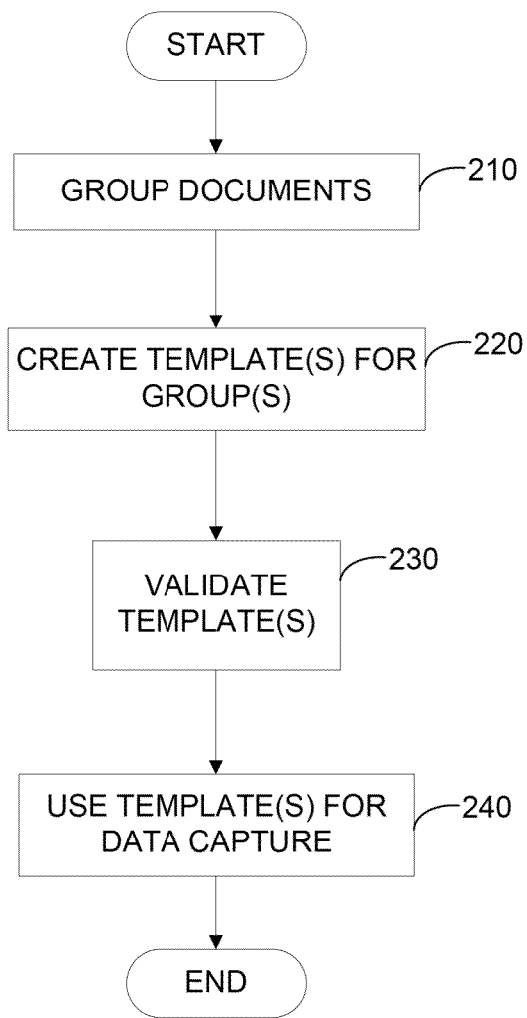
FIG. 2 is a flowchart of an illustrative process for creating a template in accordance with some embodiments of the invention.

FIG. 2 is a flow chart of a illustrative process for creating a template from received healthcare documents in a practice management system. In act 210, healthcare documents received by a practice management system from an external source are grouped into a set of documents according to one or more document characteristics. In some embodiments, only documents that were not matched to an existing template stored by the practice management system are grouped in act 210. The healthcare documents may be grouped in any suitable way, and the techniques described herein for grouping documents are merely exemplary. In some embodiments, received healthcare documents may be grouped based on classification criteria stored by the practice management system. The classification criteria may include, but are not limited to, the source of the document, the type of the document, a document classification, or a subclass of the document. For example, documents received from the same clinical provider, pharmacy, or insurance provider may be provided in one set of documents. In another example, documents belonging to the document classification "prescription" and received from a particular pharmacy may be provided in one set of documents. An exemplary subclass of the document classification "prescription" may be "prescription renewal," relating only to document for prescriptions previously prescribed but about to expire or recently expired and under consideration for renewal.

After grouping the received healthcare documents into one or more sets of documents, the process proceeds to act 220, where one of the sets of documents is selected and one or more candidate templates are created for the selected set of documents. Illustrative processes for creating a candidate template from a set of documents are discussed in further detail below. After creating candidate template(s) in act 220, the process proceeds to act 230 where the candidate template(s) are validated prior to being used for data capture.

The candidate template(s) may be validated using any suitable criteria and the techniques described herein are not limited in this respect. For example, in some embodiments, a set of documents that is analyzed to create the candidate template(s) only includes documents received for a single medical practice associated with the practice management system. Accordingly, the candidate template(s) may be representative of the documents received for that medical practice, but may not be representative of documents received from the same source, but sent to other medical practices associated with the practice management system. The inventors have recognized and appreciated that multiple medical practices associated with a practice management system often receive documents from similar sources with similar formats, allowing for an internal cross-validation of template candidate(s) prior to their use as production data capture templates. Accordingly, the candidate template(s) generated for a single medical practice may be validated by applying the template(s) to documents received in connection with other medical practices associated with the practice management system. Such a cross-validation procedure may help to eliminate candidate template(s) that are not universally representative of documents sent by a particular source. The process then proceeds to act 240, where validated candidate template(s) are provided as production templates that are used for automatic data capture, as described in more detail below.

In some embodiments, prior to identifying a set of documents from which to generate a candidate template, healthcare documents received by the practice management system may be converted into electronic form by parsing the received documents using one or more algorithms. For example, a healthcare document received via fax may be processed using an optical character recognition (OCR) engine to produce a textual representation of the healthcare document. Any suitable OCR engine may be used and the techniques described herein are not limited in this respect. For example, the open source Tesseract OCR engine or any other suitable OCR engine may be used to generate a textual representation of a received healthcare document. In some embodiments, the textual representation output from the OCR engine may include a data structure comprising individual characters and their corresponding bounding boxes, wherein the bounding boxes describe the location of the characters on the document.

After identifying individual characters in a received document, some embodiments analyze the textual information to assemble the individual characters into words and lines based on the proximity of the identified characters in the document to produce structured OCR output. The structured OCR output may be stored in a data structure that includes words in the document and corresponding bounding boxes that describe the location of the words on the document. Any suitable process for assembling individual characters into words and lines may be used and the techniques described herein are not limited in this respect. In some embodiments, both the unassembled individual characters and their corresponding bounding boxes, and the structured OCR output describing words and lines and their locations on the document may be stored. In other embodiments, only the structured OCR output is stored, while the OCR engine output is discarded. The unstructured OCR output and/or the structured OCR output may then be used to identify "captureboxes" based, at least in part, on structured data associated with the document, wherein the captureboxes represent locations on the document where at least some of the structured data is located, as discussed in more detail below.

FIG. 3 shows an illustrative healthcare document 300 received by a practice management system via a fax interface. Healthcare document 300 includes header information 310 that describes identifying information for the document including the external source which provided the document and when the document was received by the practice management system. Healthcare document 300 also includes patient information fields, including patient name field 312, date of birth field 314, and gender field 316, and provider information fields including provider name field 320. In some embodiments, healthcare documents (e.g., healthcare document 300) are processed to determine the location of particular fields on a healthcare document such as patient information fields and provider information fields to create a template candidate, as discussed in more detail below.

In some embodiments, one or more healthcare documents received by a practice management system are associated with structured data that describes information that was manually entered into the practice management system by a user. The structured data may be associated with a corresponding healthcare document in any suitable way. For example, the structured data may be represented in a data structure associated with the document or the structured data may be associated with a corresponding document in any other way. Additionally, the structured data may be formatted in any suitable way and the techniques described herein are not limited in this respect. The structured data may include, but are not limited to, patient information such as a patient's name, date of birth, and gender, and provider information such as the name of the provider. As discussed in further detail below, structured data associated with the document may be used to identify captureboxes on the document, wherein the captureboxes represent possible locations on a template for automatic data capture.

Figure 4:
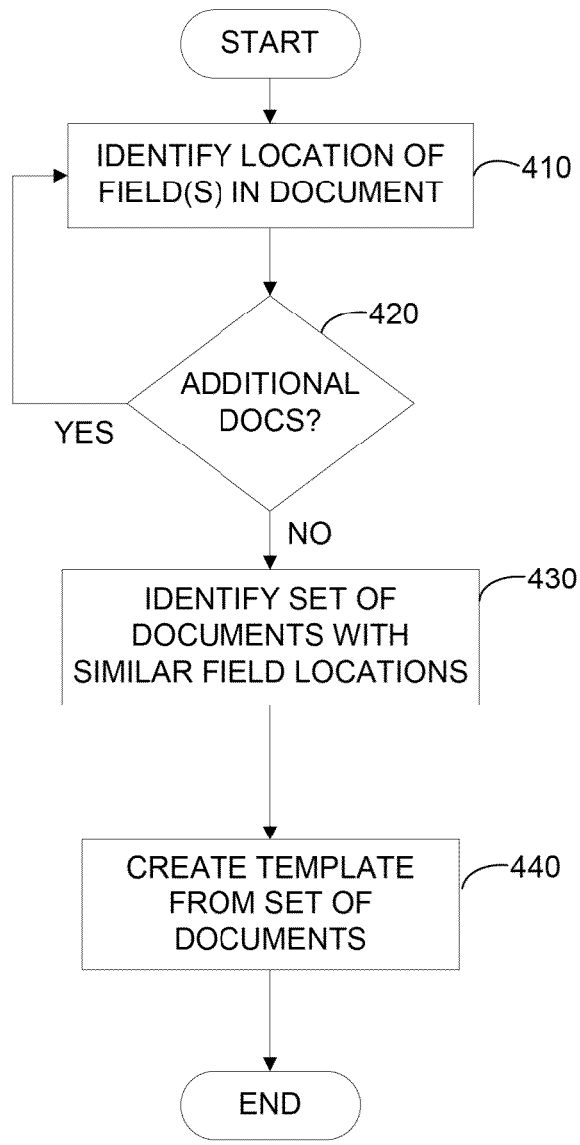
FIG. 4 is a flowchart of an illustrative process for creating a template from a set of documents in accordance with some embodiments of the invention.

FIG. 4 illustrates a technique for processing documents in a set of documents to identify a subset of documents in the set with similar characteristics. In some embodiments, the subset of documents may include all documents in the set of documents, although in other embodiments, the subset of documents may include fewer than all of the documents in the set of documents. The identified subset of documents may then be further processed to generate one or more candidate templates in accordance with the techniques described herein, and as discussed in further detail below.

In act 410, a first document in the set of documents is processed to identify locations of a plurality of fields in the document and/or a format for the plurality of fields in the document. In some embodiments, the locations of the plurality of fields are identified by locating text in the structured data associated with the first document. For example, structured data associated with healthcare document 300 may be a data structure that includes the text "Carbone, Dolores" for patient name, "07/26/1945" for date of birth, and "McFarland, Dudley" for provider name. In act 410, the structured OCR output associated with the first document may be processed to determine locations on the document that include text corresponding to the text identified in the structured data. For example, the structured OCR output may be searched for the text "Carbone, Dolores" and the bounding box corresponding to this text as represented in the structured OCR output may be identified as a bounding box (e.g., a capturebox) for a data field in the document in which the patient name included in the structured data was entered.

In some embodiments, the structured OCR output may be searched for text having content related to that in the associated structured data, but in a different format. For example, rather than searching only for text in the structured OCR output corresponding to the patient name "Carbone, Dolores," the structured OCR output may also be searched for text corresponding to "Dolores Carbone," "D. Carbone," "Dolores" in one field and "Carbone" in another field, or any other combination of the patient's first and last name. As another example, for the date, "7/26/1945" the structured OCR output may also be searched for text corresponding to "7-26-1945," "7/26/45," "July 26, 1945," "JUL 26 1945," or another suitable format for the date. Information about the standard format of particular fields on the document may be stored as part of a template candidate generated in accordance with the techniques described herein.

In some embodiments, at least some of the structured data associated with a document may be validated prior to being used for searching structured OCR output of the document. The validation of structured data may be performed in any suitable way including comparing the structured data with information stored by the practice management system. For example, if the structured data includes a patient name, a list of patients for the medical practice associated with the corresponding document may be searched to determine whether the patient name in the structured data matches any of the patients of the medical practice. Realizing that the structured data includes manually entered data that may include errors, some embodiments may not require exact matches between structured data and information stored by the practice management system for validation. Rather, some embodiments may determine that matches that differ in only a few characters are valid matches and the structured data may be used to search the structured OCR output in accordance with the techniques described herein.

FIG. 5 shows another illustration of healthcare document 300 on which three captureboxes have been identified in accordance with the techniques described herein. Patient name capturebox 510 corresponds to text identified in the structured data as a patient name, date of birth capturebox 512 corresponds to text identified in the structured data as a patient date of birth, and capturebox 514 corresponds to text identified in the structured data as a provider name.

After determining locations for captureboxes in a document, the process proceeds to act 420, where it is determined whether there are additional documents in the set to analyze. If it is determined in act 420 that there are additional documents to analyze, the process returns to act 410 to identify capturebox locations on a next document in the set. If it is determined in act 420 that all documents in the set have been analyzed, the process proceeds to act 430, where documents having captureboxes in similar document locations are identified as a set of documents from which a template can be created. Determining the set of documents having captureboxes in similar locations may be performed in any suitable way including comparing the coordinates of the captureboxes across multiple documents in the set based on the bounding box information specified in the structured OCR data associated with each document.

After determining a set of documents having captureboxes in similar locations, the process proceeds to act 440, where a candidate template is created for the set of documents identified in act 430. In addition to including locations for captureboxes, a candidate template may also include locations for a plurality of fields that describe common text elements of the set of documents. For simplicity, these fields that describe common text elements of the set of documents are called "anchorboxes" herein. Because the anchorboxes describe common text elements across the set of documents rather than values for data capture, the anchorboxes are primarily used to determine whether the template should be applied to a new healthcare document received by the practice management system, after it has been determined that the template candidate is ready for use in automatic data capture.

FIG. 6 illustrates an overlay of portions of documents in a set of documents that have been identified as having captureboxes in similar locations, as described above. As is evident from the overlay in FIG. 6, some text elements are consistently represented in the same (or very similar) location across the set of documents, whereas other text elements, which appear blurry in the overlay are not consistently represented in similar locations across the set of documents. Text elements that are consistently represented in similar locations across documents (e.g., text elements in FIG. 6 that are less blurry) may be identified as anchorbox candidates. It should be appreciated the graphical depiction of FIG. 6 to identify common text elements across a set of documents is provided merely for illustrative purposes and common text elements across documents may be identified in any suitable way including, but not limited to, analyzing structured OCR output associated with documents in the set of documents to identify the common text elements. It should also be appreciated that although the overlay illustrated in FIG. 6 may not be used in automatic template generation in accordance with the techniques described herein, such an overlay may be a useful tool in manual template construction, as it may enable a human to find suitable anchorboxes quickly by identifying portions of the overlay image that are less blurry.

In some embodiments, anchorbox candidates may be specified in a template candidate as an anchorbox in response to determining that the common text element associated with the anchorbox candidate is present on a number of documents in the set of documents that is above a threshold value. For example, a rule may specify that an anchorbox candidate may be added to the template candidate as an anchorbox only when 80% of the documents in the set include the common text element associated with the anchorbox candidate. It should be appreciated that a rule based on an 80% threshold value is only exemplary and any suitable value for determining when to include an anchorbox candidate as an anchorbox on a template may alternatively be used.

FIG. 7 shows another illustration of healthcare document 300 on which a plurality of anchorboxes have been identified in accordance with the techniques described herein. Anchorboxes 710, 712, and 714 are identified in the header information section of healthcare document 300, anchorboxes 718, 720, 722, 724, 726, 728, 730, and 732 are identified in the patient section of healthcare document 300, and anchorboxes 734, 736, 738, and 740 are identified in the provider section of healthcare document 300. Captureboxes 750, 752, 754, and 756 are also illustrated on the template overlay shown in FIG. 7.

In some embodiments, a template candidate generated by the techniques described herein may not include captureboxes in particular locations as illustrated in FIG. 7. Rather, each anchorbox identified in the template may be associated with a capturebox located in close proximity to the anchorbox (e.g., below or to the right of the anchorbox), and these captureboxes may be used to identify locations on the document for automatic data capture. Such captureboxes may be referred to as "relative captureboxes" in that they are relatively positioned with respect to anchorboxes rather than being globally or absolutely positioned. As discussed above, in some embodiments, newly created template candidates are subjected to a validation process prior to their use as production templates. Exemplary validation processes are discussed in more detail below.

Figure 8:
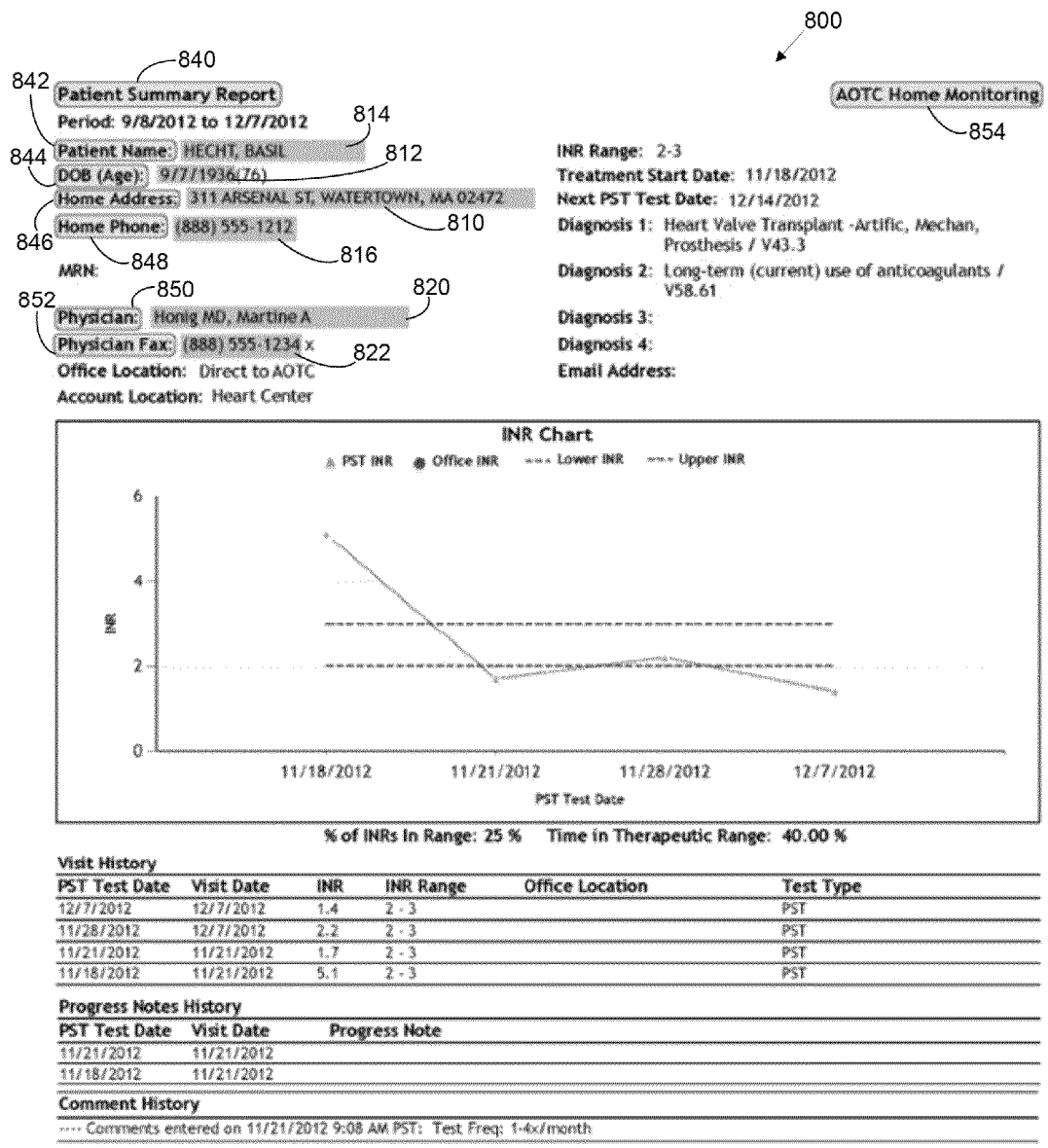
FIG. 8 is another illustrative healthcare document that may be processed in accordance with some embodiments of the invention.

FIG. 8 shows another illustrative healthcare document 800 received by a practice management system related to patient blood testing. Overlaid on healthcare document 800 is a template candidate that includes locations and/or formats of captureboxes and anchorboxes that have been identified in accordance with the techniques described herein. For example, captureboxes corresponding to patient information are identified on the template as address capturebox 810, date of birth capturebox 812, name capturebox 814, and phone capturebox 816. Captureboxes corresponding to provider information include provider name capturebox 820 and provider fax number 822. An analysis of the common text elements across documents in a set resulted in the identification of anchorboxes 840, 842, 844, 846, 848, 850, 852, and 854.

FIG. 9 shows another illustrative healthcare document 900 received by a practice management system from a pharmacy. Overlaid on healthcare document 900 is a template candidate that includes locations and/or formats of captureboxes and anchorboxes that have been identified in accordance with the techniques described herein. Captureboxes corresponding to patient information include patient name capturebox 910, address captureboxes 912 and 914, date of birth capturebox 916, and patient phone capturebox 918. Provider name capturebox 920 is also identified. An analysis of common text features across a set of documents similar to healthcare document 900 identified anchorboxes 930, 932, 934, 936, 938, 940, 942, 944, 946, 948, and 950.

FIG. 10 shows another illustrative healthcare document 1000 received by a practice management system corresponding to a prior authorization request. Overlaid on healthcare document 1000 is a template candidate that includes locations of captureboxes and anchorboxes that have been identified in accordance with the techniques described herein. Captureboxes corresponding to patient information include patient name capturebox 1010, date of birth capturebox 1012, address capturebox 1014, and patient phone capturebox 1016. Prescriber name capturebox 1020 and service provider captureboxes 1030, 1032, 1034, and 1036 are also identified. An analysis of common text features across a set of documents similar to healthcare document 1000 identified anchorboxes 1050, 1052, 1054, 1056, 1058, 1060, 1062, 1064, 1066, 1068, 1070, 1072, 1074, and 1076.

In some embodiments, a number of anchorboxes on a template candidate may be reduced prior to use of the template candidate as a production template. Any suitable process for reducing a number of anchorboxes may be used and the techniques described herein are not limited in this respect. For example, in some embodiments, only anchorbox candidates identified on every document of the set of documents may be maintained as an anchorbox on the template candidate. Additionally, in some embodiments, a maximum number of anchorboxes on a candidate template may be specified, and anchorbox candidates identified on the fewest documents of the set of documents may be excluded until the number of anchorbox candidates is below the specified maximum number of anchorboxes.

Figure 11:
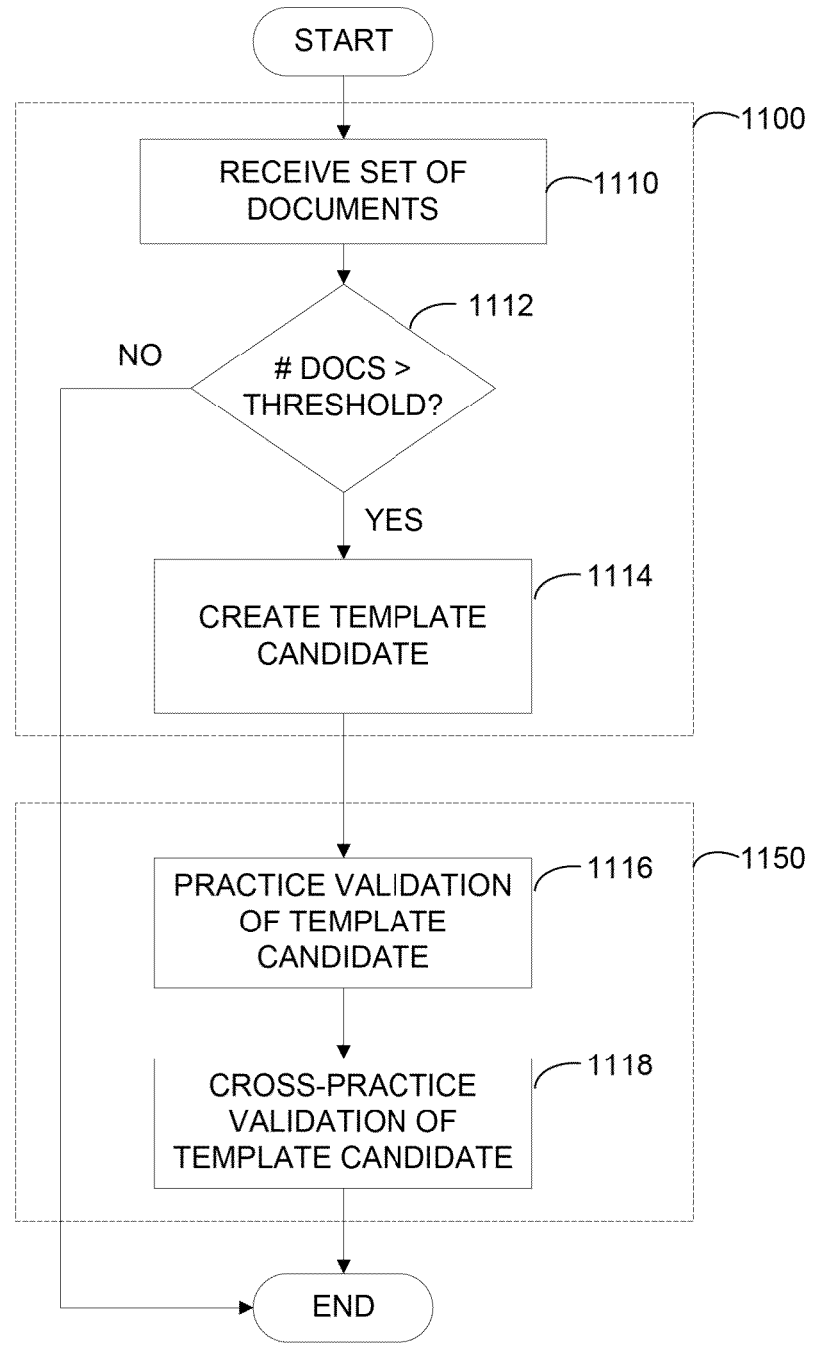
FIG. 11 is a flowchart of an illustrative process for creating a production template in accordance with some embodiments of the invention.

As discussed above, in some embodiments, after a template candidate has been created, the template candidate may undergo a validation process prior to being used as a production template with newly received healthcare documents. FIG. 11 is a flowchart of an illustrative process for creating a production template for automatic data capture in accordance with some embodiments of the invention. The illustrative process in FIG. 11 includes a template candidate generation stage 1100 followed by a template candidate verification stage 1150. Exemplary details for creating a template candidate in accordance with the techniques described herein are provided in the description above, and are briefly described below.

In the template candidate generation stage 1100, a set of documents is received in act 1110. For example, a set of documents with similar characteristics may be identified in accordance with the techniques described above. The process then proceeds to act 1112 where it is determined whether a number of documents in the set of documents is greater than a threshold value. For example, in some embodiments, only sets of documents having at least five documents may be processed to determine a template candidate for the set of documents. Any suitable threshold value may be used to establish a minimum number of documents in the set of documents required to create a template from the set of documents and the techniques described herein are not limited by the threshold value that is selected. If it is determined that the number of documents does not exceed the threshold value, the process ends. Otherwise, the process proceeds to act 1114, where a template candidate is created in accordance with the techniques described above. Exemplary template candidates, such as those illustrated in FIGS. 7-10, may include anchorboxes that identify common text features across the set of documents used to create the template candidate, and captureboxes that describe the locations on the template candidate for performing automatic data capture. In some embodiments, the locations of the captureboxes may be determined based, at least in part, on the locations of the anchorboxes.

After a template candidate has been created, the process proceeds to the candidate template validation stage 1150 to determine whether the template candidate is suitable for performing automatic data capture on newly-received healthcare documents. As discussed above, in some embodiments, a template candidate is created based only on documents for a single medical practice. In act 1116, the template candidate may be validated by processing documents received for that single medical practice using the template candidate. Depending on the performance of the template candidate in correctly identifying documents and/or performing automatic data capture using the documents for the medical practice associated with the template candidate, the process may proceed to act 1118, where the template candidate is subjected to a cross-practice validation procedure. If it is determined that the template candidate does not correctly identify and/or capture data from documents in its corresponding medical practice with sufficient accuracy, then the template candidate may be discarded. Any measure of sufficient accuracy may be used and the techniques described herein are not limited in this respect. Rather than being discarded, in some embodiments, the template candidate may form a starting template for a template to be manually created by a user for automatic data capture.

In act 1118, the template candidate is cross-validated using documents received by the practice management system for medical practices other than the medical practice for which the template candidate was created. If the performance of the template candidate during the cross-validation procedure is sufficiently accurate in identifying matching documents and/or performing accurate data capture, the template candidate is determined to be a production candidate that may then be used by the practice management system for automatic data capture on documents received in the future. Performance of a template candidate during cross-validation may be determined in any suitable way using any suitable metric. For example, in some embodiments, the performance of a template candidate may be evaluated based, at least in part, on whether the template candidate generates false positives (e.g., selects a document not suited for data capture with the template). Embodiments are not limited by the number of production templates that are created and/or used by the practice management system and any suitable number of templates including a single template or thousands of templates may be used.

Figure 12:
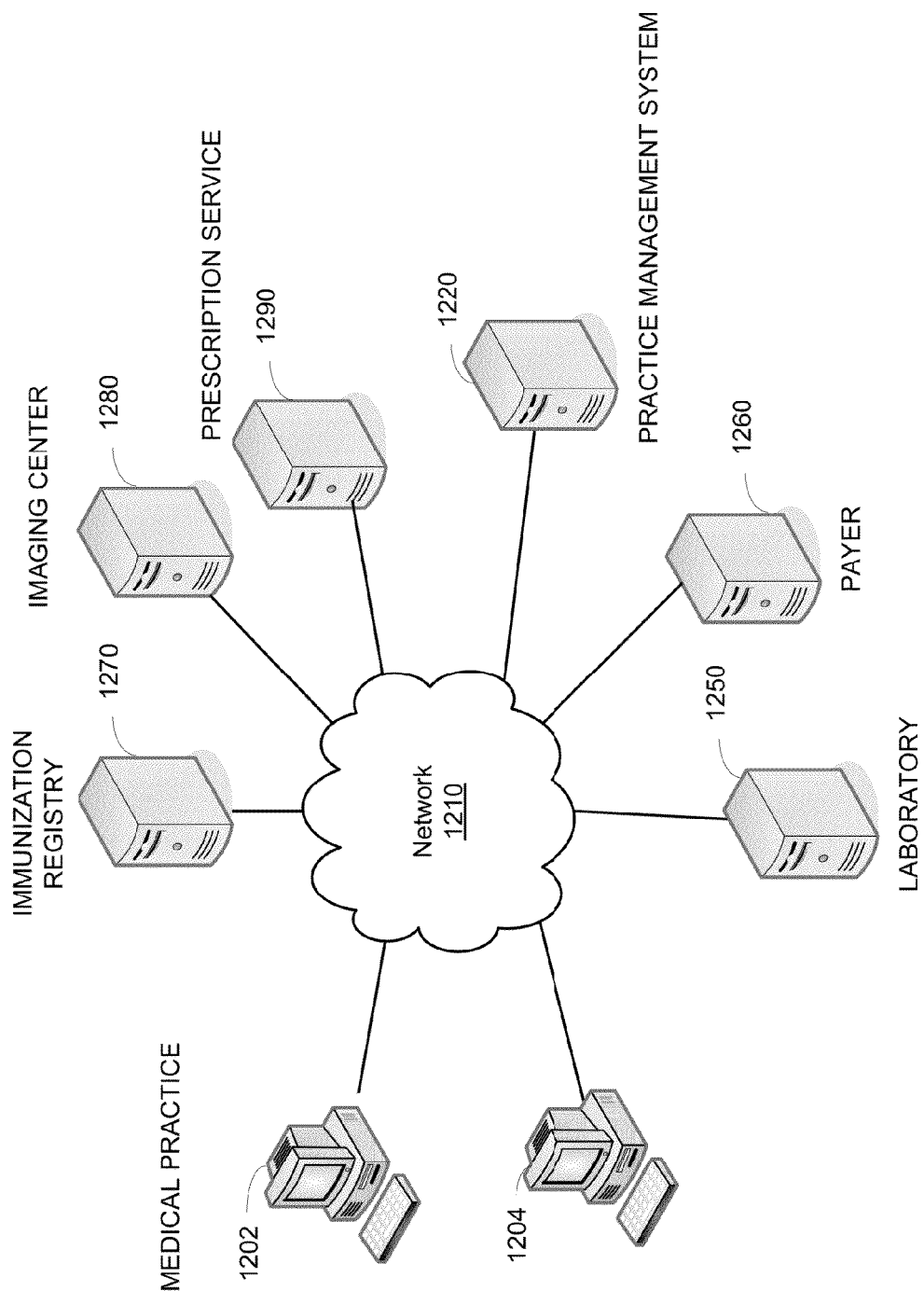
FIG. 12 is a schematic of an illustrative computer system on which some embodiments of the invention may be employed.

FIG. 12 illustrates an exemplary networked system on which some embodiments of the invention may be employed. Networked computers 1202 and 1204 located at a medical practice, and computer 1220 located at a location associated with a practice management system, are shown connected to a network 1210. Additionally, external service providers including laboratory 1250, payer 1260, immunization registry 1270, imaging center 1280, and prescription service 1290, are also shown connected to network 1210. Network 1210 may be any type of local or remote network including, for example, a local area network (LAN) or a wide area network (WAN) such as the Internet. In the example of FIG. 12, two networked computers at a medical practice and five external service providers are shown. However, it should be appreciated that network 1210 may interconnect any number of computers of various types and the networked system of FIG. 12 is provided merely for illustrative purposes. For example, computer 1220 may be connected via network 1210 (or other networks) to a plurality of computers at a plurality of medical practice locations to provide practice management services to each of the connected medical practices. As should be appreciated from the foregoing, embodiments of the invention may be employed in a networked computer system regardless of the type or network size or configuration. Additionally, one or more of the computers in the networked system may be protected from unauthorized access using any suitable security protection devices or processes including, but not limited to, firewalls, data encryption, and password-protected storage.

The above-described embodiments of the present invention can be implemented in any of numerous ways. For example, the embodiments may be implemented using hardware, software or a combination thereof. When implemented in software, the software code can be executed on any suitable processor or collection of processors, whether provided in a single computer or distributed among multiple computers. It should be appreciated that any component or collection of components that perform the functions described above can be generically considered as one or more controllers that control the above-discussed functions. The one or more controllers can be implemented in numerous ways, such as with dedicated hardware, or with general purpose hardware (e.g., one or more processors) that is programmed using microcode or software to perform the functions recited above.

In this respect, it should be appreciated that one implementation of the techniques described herein comprises at least one non-transitory computer-readable storage medium (e.g., a computer memory, a USB drive, a flash memory, a compact disk, a tape, etc.) encoded with a computer program (i.e., a plurality of instructions), which, when executed on a processor, performs the above-discussed functions. The computer-readable storage medium can be transportable such that the program stored thereon can be loaded onto any computer resource to implement the aspects of the present invention discussed herein. In addition, it should be appreciated that the reference to a computer program which, when executed, performs the above-discussed functions, is not limited to an application program running on a host computer. Rather, the term computer program is used herein in a generic sense to reference any type of computer code (e.g., software or microcode) that can be employed to program a processor to implement the above-discussed aspects of the techniques described herein.

Various techniques described herein may be used alone, in combination, or in a variety of arrangements not specifically discussed in the embodiments described in the foregoing and are therefore not limited in their application to the details and arrangement of components set forth in the foregoing description or illustrated in the drawings. For example, aspects described in one embodiment may be combined in any manner with aspects described in other embodiments.

Also, embodiments of the invention may be implemented as one or more methods, of which an example has been provided. The acts performed as part of the method(s) may be ordered in any suitable way. Accordingly, embodiments may be constructed in which acts are performed in an order different than illustrated, which may include performing some acts simultaneously, even though shown as sequential acts in illustrative embodiments.

Use of ordinal terms such as "first," "second," "third," etc., in the claims to modify a claim element does not by itself connote any priority, precedence, or order of one claim element over another or the temporal order in which acts of a method are performed. Such terms are used merely as labels to distinguish one claim element having a certain name from another element having a same name (but for use of the ordinal term).

The phraseology and terminology used herein is for the purpose of description and should not be regarded as limiting. The use of "including," "comprising," "having," "containing", "involving", and variations thereof, is meant to encompass the items listed thereafter and additional items.

Having described several embodiments of the invention in detail, various modifications and improvements will readily occur to those skilled in the art. Such modifications and improvements are intended to be within the spirit and scope of the invention. Accordingly, the foregoing description is by way of example only, and is not intended as limiting.

What is claimed is:

1. A method of generating a template for automatic data capture by analyzing a plurality of documents received by a practice management system, the method comprising:
   determining, with at least one processor, locations of a plurality of data fields in a first document of the plurality of documents, wherein the plurality of data fields are identified based, at least in part, on structured data associated with the first document;
   identifying at least one second document of the plurality of documents that includes the plurality of data fields in locations similar to those determined for the first document, wherein the first document and the at least one second document form a set of documents, wherein documents in the set of documents are received for a first medical practice of a plurality of medical practices associated with the practice management system;
   identifying common text elements located at similar locations on at least some of the documents in the set;
   determining locations of a plurality of anchorboxes, wherein the location of each of the plurality of anchorboxes corresponds to a location of one of the identified common text elements located at similar locations on at least some of the documents in the set;
   generating the template for automatic data capture, wherein the template describes the locations of the plurality of anchorboxes and the locations of the plurality of data fields on the template; and
   validating the generated template across documents received for at least two of the plurality of medical practices associated with the practice management system.

2. The method of claim 1, further comprising:
   grouping the plurality of documents based on classification criteria selected from the group consisting of document source, document class, and document subclass; and
   wherein generating the template comprises generating a separate template for each group of the plurality of documents.

3. The method of claim 1, further comprising:
   determining whether a number of documents in the set of documents exceeds a threshold value; and
   generating the template only when the number of documents in the set of documents exceeds the threshold value.

4. The method of claim 1, further comprising:
   receiving a healthcare document;
   determining whether the healthcare document includes common characteristics with the generated template; and
   performing automatic data capture using the generated template in response to determining that the healthcare document includes common characteristics with the generated template.

5. The method of claim 4, wherein determining whether the healthcare document includes common characteristics with the generated template comprises determining whether the healthcare document includes particular text in locations specified by at least one anchorbox specified by the generated template.

6. The method of claim 4, wherein performing automatic data capture comprises:
   determining locations of the plurality of data fields on the healthcare document based on the generated template; and
   capturing data values from the healthcare document located at the determined locations.

7. The method of claim 6, further comprising:
   providing the captured data values to an electronic health record stored by the practice management system.

8. A computer system providing a practice management system, the computer system comprising:
   at least one processor programmed to:
      determine locations of a plurality of data fields in a first document of a plurality of documents received by the practice management system, wherein the plurality of data fields are identified based, at least in part, on structured data associated with the first document;
      identify at least one second document of the plurality of documents that includes the plurality of data fields in locations similar to those determined for the first document, wherein the first document and the at least one second document form a set of documents, wherein documents in the set of documents are received for a first medical practice of a plurality of medical practices associated with the Practice management system;

identify common text elements located at similar locations on at least some of the documents in the set;

determine locations of a plurality of anchorboxes, wherein the location of each of the plurality of anchorboxes corresponds to a location of one of the identified common text elements located at similar locations on at least some of the documents in the set;

generate the template for automatic data capture, wherein the template describes the locations of the plurality of anchorboxes and the locations of the plurality of data fields on the template; and validate the generated template across documents received for at least two of the plurality of medical practices associated with the practice management system.

9. The computer system of claim 8, further comprising:
a communications interface configured to receive the plurality of documents; and
wherein the at least one processor is further programmed to:
group the plurality of documents based on classification criteria selected from the group consisting of document source, document class, and document subclass; and
wherein generating the template comprises generating a separate template for each group of the plurality of documents.

10. The computer system of claim 8, wherein the at least one processor is further programmed to:
determine whether a number of documents in the set of documents exceeds a threshold value; and
generate the template only when the number of documents in the set of documents exceeds the threshold value.

11. The computer system of claim 8, wherein the at least one processor is further programmed to:
analyze a healthcare document to determine whether the healthcare document includes common characteristics with the generated template; and
perform automatic data capture using the generated template in response to determining that the healthcare document includes common characteristics with the generated template.

12. The computer system of claim 11, wherein determining whether the healthcare document includes common characteristics with the generated template comprises determining whether the healthcare document includes particular text in locations specified by at least one anchorbox specified by the generated template.

13. The computer system of claim 10, wherein performing automatic data capture comprises:
determining locations of the plurality of data fields on the healthcare document based on the generated template; and
capturing data values located at the determined locations.

14. The computer system of claim 13, wherein the at least one processor is further programmed to:
provide the captured data values to an electronic health record stored by the practice management system.

15. At least one non-transitory computer-readable storage medium encoded with a plurality of instructions that, when executed by at least one computer perform a method, the method comprising:
determining locations of a plurality of data fields in a first document of a plurality of documents received by a practice management system, wherein the plurality of data fields are identified based, at least in part, on structured data associated with the first document;
identifying at least one second document of the plurality of documents that includes the plurality of data fields in locations similar to those determined for the first document, wherein the first document and the at least one second document form a set of documents, wherein documents in the set of documents are received for a first medical practice of a plurality of medical practices associated with the practice management system;
identifying common text elements located at similar locations on at least some of the documents in the set;
determining locations of a plurality of anchorboxes, wherein the location of each of the plurality of anchorboxes corresponds to a location of one of the identified common text elements located at similar locations on at least some of the documents in the set;
generating the template for automatic data capture, wherein the template describes the locations of the plurality of anchorboxes and the locations of the plurality of data fields on the template; and
validating the generated template across documents received for at least two of the plurality of medical practices associated with the practice management system.

16. The at least one computer-readable storage medium of claim 15, wherein the method further comprises:
grouping the plurality of documents based on classification criteria selected from the group consisting of document source, document class, and document subclass; and
wherein generating the template comprises generating a separate template for each group of the plurality of documents.

17. The at least one computer-readable storage medium of claim 15, wherein the method further comprises:
determining whether a number of documents in the set of documents exceeds a threshold value; and
generating the template only when the number of documents in the set of documents exceeds the threshold value.

18. The at least one computer-readable storage medium of claim 15, wherein the method further comprises:
receiving a healthcare document;
determining whether the healthcare document includes common characteristics with the generated template; and
performing automatic data capture using the generated template in response to determining that the healthcare document matches the generated template.

19. The at least one computer-readable storage medium of claim 18, wherein determining whether the healthcare document includes common characteristics with the generated template comprises determining whether the healthcare document includes particular text in locations specified by at least one anchorbox specified by the generated template.

20. The at least one computer-readable storage medium of claim 18, wherein performing automatic data capture comprises:

determining locations of the plurality of data fields on the healthcare document based on the generated template; and capturing data values from the healthcare document located at the determined locations.

21. The at least one computer-readable storage medium of claim 20, wherein the method further comprises:

providing the captured data values to an electronic health record stored by the practice management system.

* * * * *